US009296702B2

(12) United States Patent
Scallen

(10) Patent No.: US 9,296,702 B2
(45) Date of Patent: Mar. 29, 2016

(54) ROSUVASTATIN ENANTIOMER COMPOUNDS

(71) Applicant: Terence J. Scallen, Silver Bay, MN (US)

(72) Inventor: Terence J. Scallen, Silver Bay, MN (US)

( * ) Notice: Subject to any disclaimer, the term of this patent is extended or adjusted under 35 U.S.C. 154(b) by 0 days.

(21) Appl. No.: 14/256,584

(22) Filed: Apr. 18, 2014

(65) Prior Publication Data

US 2014/0243528 A1    Aug. 28, 2014

Related U.S. Application Data

(62) Division of application No. 13/624,997, filed on Sep. 24, 2012, now Pat. No. 8,729,092.

(51) Int. Cl.
 *C07D 239/42*    (2006.01)
(52) U.S. Cl.
 CPC .................................... *C07D 239/42* (2013.01)
(58) Field of Classification Search
 CPC ...................................................... C07D 239/42
 USPC ......................................................... 544/332
 See application file for complete search history.

(56) References Cited

U.S. PATENT DOCUMENTS

| | | | |
|---|---|---|---|
| 4,346,227 A | | 8/1982 | Terahara et al. |
| 4,444,784 A | | 4/1984 | Hoffman et al. |
| 4,613,610 A | | 9/1986 | Wareing |
| 5,177,080 A | * | 1/1993 | Angerbauer et al. ......... 514/277 |
| 5,849,777 A | | 12/1998 | Scallen et al. |
| RE37,314 E | | 8/2001 | Hirai et al. |
| 2005/0187204 A1 | * | 8/2005 | Kondo et al. ................. 514/171 |

OTHER PUBLICATIONS

McTaggart et al, Am J Cardiol 2001;87(suppl):28A-28B.*
Bababeygy et al, Anticancer Research Dec. 2009 vol. 29 No. 12 4901-4908.*
Dr. Bruce, New Local, Dec. 3, 2013.*
Fallon et al, Dangers of Statin Drugs: What You Haven't Been Told About Popular Cholesterol-Lowering Medicines, Jun. 14, 2004.*
Cecil Textbook of Medicine, 20st Edition, vol. 1996.*
Maltese, Neurology. Oct. 1983; 33(10):1294-9.*
Greenberg et al, Current Issue, vol. 101 No. 16, p. 5788-5793.*
Juszczyk et al, Clinical Study, Fall 2005, p. 197-199.*
Material Safety Data Sheet, by Santa Cruz Biotechnology, Aug. 31, 2010.
McTaggart et al. "Preclinical and Clinical Pharmacology of Rosuvastatin, a New 3-Hydroxy-3-Methylglutaryl Coenzyme A Reductase Inhibitor", *Am. J. Cardiol.* 87(suppl):28B-32B.
Jonathan J. Darrow, The Patentability of Enantiomers: Implications for the Pharmaceutical Industry, Stanford Technology Law Review, 2007, pp. 2 et seq., available at http://stlr.stanford.edu/pdf/darrow-patentability.pdf.
Zdenko Casar et al., Lactone Pathway to Statins Utilizing the Wittig Reaction. The Synthesis of Rosuvastatin. Journal of Organic Chemistry, 2010, vol. 75, 6681-84.
G. Beck et al., Synthesis and Biological Activity of New HMG-CoA Reductase Inhibitors. Journal of the American Chemical Society, 1990, vol. 33(1), 52-60.

\* cited by examiner

*Primary Examiner* — Wu-Cheng Winston Shen
*Assistant Examiner* — Jean Cornet
(74) *Attorney, Agent, or Firm* — Myers Bigel & Sibley, P.A.

(57) ABSTRACT

The invention discloses a method for the treatment of diseases, particularly those diseases characterized by diminished or aberrant cellular function, including AIDS, cancer, and Alzheimer's Disease. The method comprises administering a therapeutically effective amount of rosuvastatin enantiomer compounds in their (3R, 5R), (3S, 5R), or (3S, 5S) configurations, or pharmaceutically acceptable salts thereof. Biologically-active rosuvastatin enantiomer compounds with (3R, 5R), (3S, 5R), and (3S, 5S) stereochemistry are also disclosed.

9 Claims, No Drawings

ROSUVASTATIN ENANTIOMER COMPOUNDS

CROSS-REFERENCE TO RELATED APPLICATIONS

This application is a divisional of U.S. patent application Ser. No. 13/624,997, filed Sep. 24, 2012, now allowed, the disclosure of which is incorporated by reference herein in its entirety.

FIELD OF THE INVENTION

The present invention relates to rosuvastatin enantiomer compounds having (3R, 5R), (3S, 5R), or (3S, 5S) configurations, which maximize or normalize cellular phenotypic expression and that are broadly useful in the treatment of a wide variety of human diseases, including cancer, atherosclerosis, and immune system diseases or disorders.

BACKGROUND OF THE INVENTION

Pyrimidine derivatives, including rosuvastatin compounds with a (3R, 5S) configuration, have been recognized for their ability to inhibit 3-hydroxy-3-methyl-glutaryl coenzyme A (HMG-CoA) reductase. Because HMG-CoA reductase plays a major role in the synthesis of cholesterol, these pyrimidine derivatives have been described as useful in the treatment of hypercholesterolemia, hyperlipoproteinemia, and atherosclerosis (U.S. Pat. RE 37,314). A number of other compounds have similarly been described as useful in the inhibition of HMG-CoA reductase, and thus in the treatment of atherosclerosis, including pravastatin sodium (U.S. Pat. No. 4,346,227), simvastatin (U.S. Pat. No. 4,444,784), and certain mevalonate and mevalonolactone derivatives (U.S. Pat. No. 5,849,777).

Compounds in this latter category (mevalonate and mevalonolactone derivatives) have also been recognized for their ability to modulate cell function. See U.S. Pat. No. 5,849,777, which is hereby incorporated by reference. Because abnormal cell function is associated with a number of diseases, including cancer and Acquired Immune Deficiency Syndrome (AIDS), the ability to enhance or modulate cell function is therefore of significant importance in the treatment of diseases associated with such aberrant or deficient cell function. Unfortunately, despite research efforts spanning a number of decades, modulation of cellular activity, including differentiation, is still incompletely understood, partly a result of the numerous and complex pathways by which such modulation occurs. The mevalonate and mevalonolactone derivates described in U.S. Pat. No. 5,849,777 are believed to function by modulating phenotypic expression, such as by inducing expression of unexpressed genes so as to increase cell function, and/or by normalizing cell surface membrane characteristics including the expression of oligosaccharides.

Although some compounds that inhibit HMG-CoA reductase are also useful as cell modulators, there is no apparent correlation between the inhibition of HMG-CoA reductase and cell modulation. In addition, the relevant literature has recognized the importance of distinguishing between enantiomeric forms of pharmaceutically active substances due to potential differences in pharmacologic activity as well as the difficulty in predicting the therapeutically relevant characteristics of any given enantiomeric form (Darrow, J., The Patentability of Enantiomers, Implications for the Pharmaceutical Industry, Stanford Technology Law Review, 2007, pages 2 et seq.).

SUMMARY OF THE INVENTION

The rosuvastatin enantiomer compounds of the present invention, having a (3R, 5R), (3S, 5R), or (3S, 5S) configuration, induce or enhance cellular differentiation, that is, they maximize or normalize cellular phenotypic expression. Unlike rosuvastatin compounds described in the literature (see, e.g., Z. Casar, Lactone Pathway to Statins Utilizing the Wittig Reaction. The Synthesis of Rosuvastatin. Journal of Organic Chemistry, 2010, vol. 75, pp. 6681-84), the compounds of the present invention operate via a different mechanism of action, owing to their particular stereoisomeric configuration, and thereby exhibit unexpectedly increased effectiveness and applicability to a much broader array of diseases. By modulating the phenotypic expression of cells with diminished or aberrant cellular function, the compounds of the present invention, among other things, maximize the function of immunocytes by facilitating immunological recognition and elimination from the body. They are therefore of therapeutic benefit in a range of diseases characterized by either (i) diminished cellular function or (ii) aberrant cellular function. Diseases in category (i) include infectious diseases such as Acquired Immune Deficiency Syndrome (AIDS) and hypogammaglobulenemia, and other diseases of bacterial, fungal, rickettsial, viral, or parasitic origin. Diseases in category (ii) include: autoimmune diseases such as diabetes, multiple sclerosis, lupus erythematosus, and rheumatoid arthritis; nervous system diseases such as Alzheimer's disease, Amyotrophic Lateral Sclerosis, and Parkinson's disease; and cancer.

DETAILED DESCRIPTION OF THE INVENTION

The present invention relates to compounds of the formula:

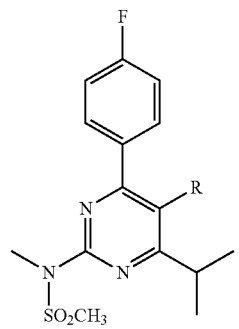

wherein R is any of the following:

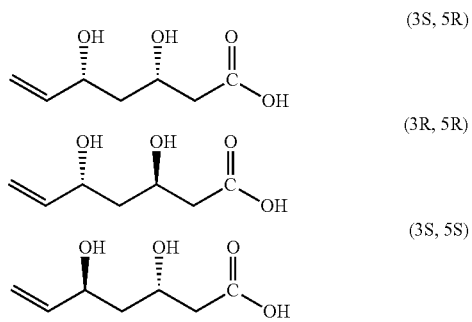

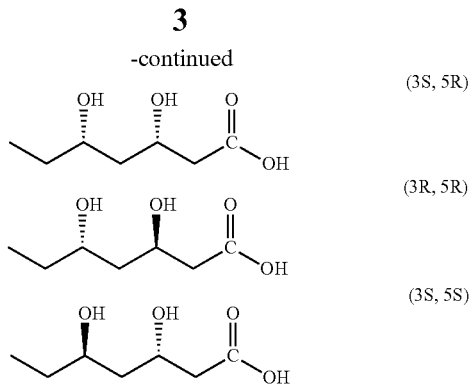

Preparation of the Invention

The compounds of the present invention can be prepared according to the methods described in U.S. RE 37,314 E, which is hereby incorporated by reference, followed by chiral resolution (separation). Resolution of racemates or other mixtures of the enantiomers can be readily accomplished by conventional procedures, as described, for example, in U.S. Pat. No. 4,613,610, which is hereby incorporated by reference. Alternatively and preferably, the desired differentiatively-active enantiomers can be synthesized by processes that yield only or substantially only the desired enantiomers. Such processes are well known in the art. While the presence of inactive or less active stereoisomeric matter is not generally detrimental, the presence of inactive or less active enantiomers must be considered when calculating dosage levels. The invention therefore includes racemic or other mixtures of any of the enantiomers described herein.

Utility of the Invention

The rosuvastatin enantiomer compounds of the present invention are contemplated to modulate cell differentiation activity across a broad array of cell types, and thus to be useful in the treatment of a number of diseases. According to the invention, cells with aberrant or deficient function are exposed in vivo or in vitro to the compounds of the invention in order to improve cell modulation activity. As used herein, "cell modulation" refers to substantially all activities of the normal mature cell that tend to differentiate that cell from other cell types, including: the bioproduction of proteins, carbohydrates, fats, cholesterol, hormones, enzymes, sugars, and immunoproducts (such as globulins and antibodies); growth regulation functions which maintain or impose normal growth patterns; and cell structure regulation functions which provide cell structures characteristic of normal cell differentiative function, such as cell membrane composition, e.g., oligopolysaccharide structure, or cytoplasmic composition. Thus, the process of the invention provides a method for the autoregulation of cellular functions comprising virtually all functions characteristic of the mature individuated cell, i.e., those functions not peculiar to early progenitor cells having a purely proliferative capability, and further provides a method for increasing biologically adequate cell differentiative activity by inducing expression of unexpressed cell differentiative capacity, for example, to diversify expression of differentiative activity, or to induce differentiative activity in immature, substantially non-individuated cells, or in abnormally differentiated cells, e.g., transformed or aberrant cells.

The term "autoregulation" as used herein refers to the utility of the modulators in restoring cellular biochemical balance to cells exhibiting abnormal differentiative activity owing to known or unknown factors; such as toxic substances introduced into the organism from the environment; biochemical imbalance of the organism caused by metabolic disturbances, diseases, or disorders; or injury to the cell, organ, or organism. The term "autoregulation" further includes the utility of the modulators in the rectification of cell activity heretofore regarded as "normal", such as arresting senescence of cells both in vivo and in vitro, and diversification of cell function with respect to existing cell function within accepted ranges of normal cell function.

The modulators of the invention accordingly function to stimulate phenotypic cell expression, including rectification of abnormal cell production, reassertion of normal cell function, correction of cellular incompetence, restoration of normal growth patterns, modulation of aberrant cell structures, reestablishment of normal cell growth patterns, and further, diversification and/or expansion of existing cell function within the genetic capabilities of the cell.

The term "abnormal", as used herein to modify differentiative activity or cell function, refers to cell differentiative activity, as described above, which is outside of accepted ranges; thus, "abnormal differentiative activity" refers to pathological cell differentiative activity manifested in cell morphology and/or activity above or below accepted standards, and which in vivo tends to result in malfunction of the organism, resulting in distress, debilitation, and/or death of the organism.

Exposure of cells to the differentiators according to the invention invokes cell mechanisms which promote normal differentiative activity or which expand or diversify cell differentiative activity. In applications wherein the differentiators are employed to improve abnormal differentiative activity at least a ten percent improvement in such function is contemplated; i.e., at least a ten percent, preferably twenty percent, improvement in the parameter of interest (with reference to the conventional measurement of such parameter) is contemplated. For example, if bioproduction of a cell is abnormally low or high, at least a ten percent increase or decrease by mass, respectively, of the product of interest over a comparable time period is contemplated. Thus, if a given leukocyte biomass produces ten nanograms of immunoglobulin G (IgG) over a one-hour period under normal in vitro conditions, the same biomass will produce at least eleven nanograms of IgG over the same time period under the same culture conditions on exposure to the modulators of the invention. By the same token, the growth rate of a biomass of malignant cells exhibiting an abnormally high growth rate is decreased by at least about ten percent on exposure to the modulators of the invention. Similarly, in vivo, rectification of abnormal cell differentiative activity of at least about ten percent is established by comparing cell or organ activity before and after exposure to the modulators of the invention, according to standard measuring techniques, such as blood determinations for the product of interest, nuclear magnetic resonance (NMR) or computed axial tomography (CAT) scans for evaluation of cellular activity, weight assessments for determination of cell growth, and a variety of other biotechnical diagnostic procedures well-known in the art.

For use of differentiators according to the invention to diversify or expand cell differentiative activity, a similar, about ten percent, preferably about twenty percent, increase in cell differentiative activity, based on conventional measurements of the parameter of interest, is contemplated. For example, exposure of stimulated murine splenocytes to the differentiators promotes the production of antibody, with at least a ten percent increase in antibody diversity with respect to affinity, avidity, and/or specificity of the antibody pool produced. With respect to modification of cell structure, at least about a ten percent change in cell structure, particularly cell component biochemical characteristics, chemical characteristics, or stereochemical arrangement of cell components, is contemplated. For example, a change in the oligosaccharide content of cell-surface membranes (as measured, for example, by lectin binding) of at least about ten percent, preferably at least about twenty percent, is contemplated. Oligosaccharide cell-surface membrane characteristics have been correlated with cell growth patterns, and a modulation of abnormal cell-surface membrane oligosaccharide content with the differentiators of the invention to provide at least about a ten percent decrease in abnormally high cell reproduction rates, or at least about a ten percent increase in abnormally low cell reproduction rates, as observed in senescent cells, for example, is within the scope of the invention. In this instance, for example, improvements in cell differentiative activity are measurable in vitro by either a change in the rate of lectin binding, reflecting a change in oligosaccharide cell-surface membrane characteristics, or by a direct measurement of cell reproduction activity, typically determined by change in generation time (Tg).

Cell modulation includes the ability to promote cytostasis, and thus to inhibit tumor growth and/or tumor metastasis. As such, the rosuvastatin enantiomer compounds of the present invention are contemplated as useful in the treatment of various tumor types including leukemias, lymphomas, melanomas, and myelomas, as well as tumors of the ovary, cervix, breast, lung, colon, stomach, liver, pancreas, bladder, prostate, brain, and larynx, among others. The compounds of the present invention may also function as anti-tumor agents by enhancing the activity of natural killer cells or other cells of the immune system, as these cells are believed to play an important role in the body's defense against tumor-transformed cells.

It is postulated that the modulators described herein influence a sufficiently primitive biochemical control process which affects the regulation of cell differentiation at a sufficiently basic level, to have a substantially universal function as a modulator of cell activity to promote normal cell differentiative function over a broad spectrum of cells. It is specifically contemplated that the modulators of the invention function to rectify abnormal production of a variety of protein, glycoprotein, carbohydrate and fat cell products, such as cholesterol, as well as enzymes; hormones, such as somatostatin, MSH (melanocyte-stimulating hormone), and pituitary hormones; immunoproducts, such as lymphokines, globulins and antigens; to reassert normal cell function, such as the normal function of liver cells; to correct cell deficiencies, such as immunodeficiencies, glandular deficiencies, such as hypothalmia, and metabolic deficiencies; to restore normal growth patterns to cells exhibiting decelerated growth rates, such as senescent cells, or accelerated growth rates, such as malignant cells; to modulate aberrant cell structures to approach those of normal cells; to stimulate progenitor and/or precursor cells into full production of mature cells; and, further, to diversify and/or expand existing cell function within the genetic capabilities of the cell, such as to increase the immunoresponse of splenocytes to antigenic stimulus, with respect to both the diversity and amount of antibodies produced.

The modulators exert biochemical control over cell differentiation processes, intervening at a very early point in cellular differentiative pathways to promote cell autoregulation of differentiative function. It is accordingly believed that the modulators described herein comprise molecules which, with respect to both biologically-active functional moieties and with respect to the presentation of these biologically-active functional groups to the cell (i.e., the stereochemistry of the molecule), function to counteract cellular imbalances (resulting in abnormal differentiative function over a broad spectrum of cells and differentiative activity). Thus, in contrast to known differentiators which tend to be relatively specific in effect, with respect to either particular cells or particular differentiative activity, the modulators of the present invention are effective in restoring normal differentiative function to chemically imbalanced cells of plants, animals (especially mammals including humans), microorganisms, viruses, and insects. Further, the modulators of the invention function to increase diversity of differentiative function within the genetic potential of the cell.

Administration of the Invention

The compounds of the present invention can be administered orally or intraparenterally, such as via intravenous or intramuscular injection. For example, the compounds of the present invention may be administered: (1) orally, such as in the form of tablets, powders, capsules or granules, aqueous or oily suspensions, or syrups or elixirs; or (2) parenterally, such as in the form of injections of aqueous or oily suspensions, or in the form of nasal sprays, aerosols, powders or suspensions. These formulations can be prepared in a conventional manner by using excipients, binders, lubricants, aqueous or oily solubilizers, emulsifiers, suspending agents, and the like. In addition, preservatives, stabilizers, or adjuvants may be used.

Appropriate dosage levels may vary with the administration route, age, weight, condition, and disease type under treatment. In general, however, when the mode of administration is via intraperitoneal or subcutaneous injection or via nasal spray, optimal dosage levels are in the range of one hundred nanograms per kilogram, administered every other day, to one hundred micrograms per kilogram, administered every other day. When the mode of administration is oral, optimal dosage levels are in the range of one nanogram per kilogram, administered every other day, to one milligram per kilogram, administered every other day. Regardless of the mode of administration, equivalent dosage levels administered on a more frequent (e.g., daily or twice daily, etc.) basis, or less frequent basis (e.g., once a week) may also be used.

Dosage of the invention appears to be critical, i.e., dosages in excess of the therapeutic dosage range are typically ineffective to increase response and may actually, for example, stimulate tumor growth, while dosages below the range are substantially ineffective, for example, in inhibiting tumor burden. The differentiators have no observed toxic side effects at therapeutic dosage levels. For humans, it is recommended that administration occur via intravenous (i.v.), intraperitoneal (i.p.), or subcutaneous injection on a regimen of at least alternate days until tumor response is noted, preferably by non-invasive diagnostic techniques such as nuclear magnetic resonance imaging (NMRI). Initial positive tumor response (such as tumor deformity or presence of tumor-associated edema) is contemplated as observable as early as about two weeks from the start of the therapeutic regimen. After substantial tumor response has been achieved, dosage frequency may be decreased to, for example, a weekly basis, until the tumor has been conquered.

In an exemplary procedure, administration of a therapeutic dosage of cytostatic compound is begun on a human tumor host on Monday of week 1. One hundred ng/kg in physiological saline is administered i.v., or i.p., Monday, Wednesday, and Friday of week 1; this procedure is repeated on continuous weeks 2, 3, 4, and following weeks with NMR monitoring on a weekly basis until the desired reduction in tumor burden is achieved. While the regimen may be continued thereafter, experimental evidence indicates that tumor rebound after treatment is not significantly incident to the therapeutic process of the invention.

Stereochemistry of the Invention

Although both the mevalonate and mevalonolactone derivatives described in U.S. Pat. No. 5,849,777 and the pyrimidine derivatives described in U.S. Pat. RE 37,314 have been recognized for their ability to inhibit HMB-CoA, there is no apparent correlation between HMG-CoA reductase inhibitory activity and promotion of cell modulation activity. The ability to modulate cell activity does, however, appear to depend on the particular chiral configuration of the 3.5 carbon atoms in the heptanoic or heptenoic acid portion of the invention. In particular, the rosuvastatin enantiomer compounds of this invention in either their (3R, 5R), (3S, 5R), or (3S, 5S) configurations, including racemates or mixtures of (3R, 5R)-(3S, 5S) or (3S, 5R)-(3R, 5S), are contemplated as having greater cell modulation activity than do related compounds having the (3R, 5S) configuration. Purified rosuvastatin enantiomers of the (3R, 5S) configuration, substantially free of the enantiomers having a (3R, 5R), (3S, 5R), or (3S, 5S) configuration, are therefore not within the scope of this invention. The conventions used herein to characterize particular stereoisomeric configurations are those commonly used in the art. See, for example, U.S. Pat. No. 4,613,610.

Clinical Applications of the Invention

The rosuvastatin enantiomer compounds described in the present invention induce or enhance cellular differentiation, i.e., they maximize and/or normalize cellular phenotypic expression. Therefore, they will be of therapeutic benefit in diseases characterized by either (1) diminished cellular function or (2) aberrant cellular function. Examples of the first category include acquired immune deficiency syndrome (AIDS) and hypogammaglobulinemia. Another example of the first category is the treatment of infectious diseases caused by pathogens of bacterial, fungal, rickettsial, viral or parasitic origin. The compounds of the invention maximize the function of immunocytes by maximizing the phenotypic expression of these cells. Therefore, immunological recognition and elimination of these pathogens from the body are facilitated by treatment using the compounds described in the invention. Patients with atherosclerosis benefit by treatment with the compounds of this invention, since phenotypic expression (differentiation) of liver cells (hepatocytes) are induced and enhanced. This leads to increased levels of the LDL receptor on the surface of hepatocytes and this facilitates the removal of cholesterol from the body. Although rosuvastatin in its (3R, 5S) configuration has previously been disclosed as useful in the treatment of atherosclerosis by inhibiting cholesterol biosynthesis at the rate-limiting step, i.e., HMG-CoA reductase, the rosuvastatin enantiomer compounds of the present invention do not inhibit cholesterol biosynthesis and are believed to achieve their utility via a different mechanism of action (enhancement of cellular differentiation, e.g., increased levels of the LDL receptor on the surface of liver cells (hepatocytes) and this facilitates removal of cholesterol from the body and, therefore, leads to a decrease in blood cholesterol. The different mechanism of action of the rosuvastatin enantiomers of the present invention—(3R, 5R), (3S, 5S), and (3S, 5R)—allows for both greater efficacy and reduced toxicity as compared to rosuvastatin compounds of the (3R, 5S) form. Also, it is known in the art that only the (3R, 5S) enantiomer inhibits cholesterol biosynthesis, making the utility of the particular enantiomers of the present invention unexpected.

Diseases of the second category, i.e., aberrant cellular function, include cancer, as well as autoimmune diseases such as diabetes, multiple sclerosis, lupus erythematosus and rheumatoid arthritis.

That which is claimed:

1. A method of treating a disease characterized by aberrant cellular function, in a human or non-human mammal, comprising administering a compound of the formula:

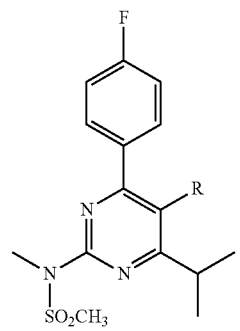

wherein R is selected from the group consisting of:
(3S,5S)-dihydroxy-(E)-6-heptenoic acid;
(3S,5R)-dihydroxy-(E)-6-heptenoic acid;
(3S,5S)-dihydroxy-(E)-6-heptanoic acid; and
(3S,5R), dihydroxy-(E)-6-heptanoic acid,
wherein the disease is selected from the group consisting of hypercholesterolemia, hyperlipidemia and atherosclerosis.

2. The method of claim 1, wherein the compound is in the form of a non-toxic pharmaceutically acceptable salt.

3. The method of claim 1, wherein the compound is in the form of a sodium salt.

4. The method of claim 1, wherein the compound is in the form of a calcium salt.

5. The method of claim 1, wherein the disease characterized by aberrant cellular function is hypercholesterolemia.

6. The method of claim 1, wherein the disease characterized by aberrant cellular function is hyperlipidemia.

7. The method of claim 1, wherein the disease characterized by aberrant cellular function is atherosclerosis.

8. The method of claim 1, wherein the compound is administered via intraperitoneal or subcutaneous injection or via nasal spray, and in which the dose range is one hundred nanograms per kilogram to one hundred micrograms per kilogram, administered every other day.

9. The method of claim 1, wherein the compound is administered orally, and in which the dose range is one nanogram per kilogram to one milligram per kilogram, administered every other day.

* * * * *